(12) United States Patent
McMillan et al.

(10) Patent No.: US 7,786,441 B2
(45) Date of Patent: Aug. 31, 2010

(54) TENSIOGRAPHIC DROPHEAD

(76) Inventors: Norman McMillan, Whitebutts Killeshin Road, Craiguecullen County Carlow, Carlow (IE); Stuart Smith, Baltyboys, County Wicklow, Blessington (IE); Michael Baker, Chapelstown, County Carlow, Carlow (IE)

( * ) Notice: Subject to any disclaimer, the term of this patent is extended or adjusted under 35 U.S.C. 154(b) by 30 days.

(21) Appl. No.: 11/884,636

(22) PCT Filed: Feb. 20, 2006

(86) PCT No.: PCT/US2006/060118

§ 371 (c)(1),
(2), (4) Date: Aug. 8, 2008

(87) PCT Pub. No.: WO2007/048124

PCT Pub. Date: Apr. 26, 2007

(65) Prior Publication Data

US 2009/0200475 A1    Aug. 13, 2009

(30) Foreign Application Priority Data

Feb. 18, 2005   (IR) .............................. S2005/0091

(51) Int. Cl.
*G01J 5/02* (2006.01)

(52) U.S. Cl. .................................... 250/341.2; 250/393
(58) Field of Classification Search ............. 250/341.2, 250/393, 227.29, 573, 574, 575, 576
See application file for complete search history.

(56) References Cited

U.S. PATENT DOCUMENTS 4,910,402 A * 3/1990 McMillan ................. 250/341.2

FOREIGN PATENT DOCUMENTS

EP        364203 A * 4/1990

* cited by examiner

*Primary Examiner*—David P Porta
*Assistant Examiner*—Mark R Gaworecki
(74) *Attorney, Agent, or Firm*—Whiteford, Taylor & Preston LLP; Jeffrey C. Maynard (57) ABSTRACT

A tensiographic drophead comprises a quartz body 10 having a terminal surface 18 with a peripheral drop suspension edge 20. A liquid feed bore 14 extends through the body for supplying a liquid to the terminal surface to form a drop 32 whose outer edges are suspended from the suspension edge 20. At least two light guides 26, 28 extend through the body for respectively transmitting light into and collecting light reflected internally from the drop. The light guides terminate above the plane containing the suspension edge such that the intensity of the reflected light has a significant second order reflection peak.

16 Claims, 13 Drawing Sheets

TENSIOGRAPHIC DROPHEAD

TECHNICAL FIELD

This invention relates to a tensiographic drophead.

BACKGROUND ART

U.S. Pat. No. 4,910,402 describes various forms of apparatus wherein a static or dynamic drop of a liquid is formed suspended from the ends of a pair of light guides so that light can be directed into the drop from one light guide and collected in the other light guide (the term "light" is intended herein to include UV and IR as well as visible light). This allows many different types of measurement to be made on the liquid, as described in that patent.

The part of the apparatus near the lower ends of the two light guides, i.e. where the drop is formed, is referred to as a tensiographic drophead. In FIG. 3 of U.S. Pat. No. 4,910,402 the drophead is shown as a simple glass cylinder within which the light guides are secured in their desired relative positions by embedding them in epoxy resin. Although effective at the time, and still suitable for many measurements, there is a need for an improved drophead which will allow greater accuracy and reproducibility of results.

DISCLOSURE OF THE INVENTION

The invention provides a tensiographic drophead comprising a body having a terminal surface with a peripheral edge substantially disposed in a plane, a liquid feed bore extending through the body to the terminal surface for transporting liquid to or from the terminal surface to thereby control, in use, the volume of a drop whose outer edges are defined by the peripheral edge, a light source for transmitting light into the drop, said light source having a transmission surface, and a light detector for collecting light reflected internally from the drop back to the drophead, said light detector having a collection surface, wherein the transmission surface and the collection surface are each disposed in the drophead and are each spaced apart from said plane of said peripheral edge.

BRIEF DESCRIPTION OF THE DRAWINGS

Embodiments of the invention will now be described, by way of example, with reference to the accompanying drawings, in which.

DETAILED DESCRIPTION OF PREFERRED EMBODIMENTS

In the description and claims expressions of orientation refer to the orientation of the drophead in use. As explained below, many dropheads can be used in a "normal" orientation where the drops are pendant, or in an inverted orientation where the drops are sessile. Terms such as lower, upper, above and below are used with respect to the "normal" orientation and it is this orientation used in the Figures to illustrate the dropheads.

Figure 1:
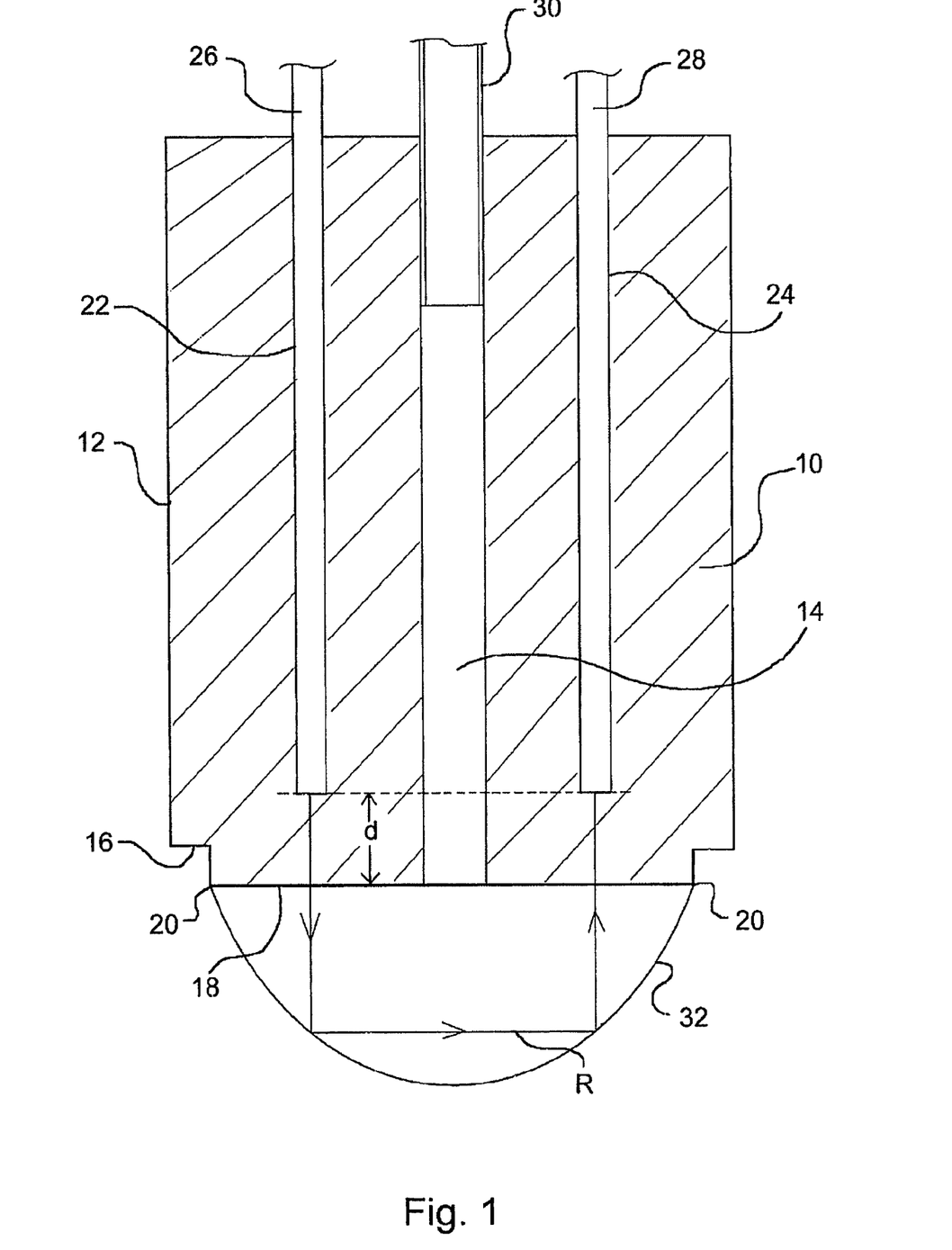
FIG. 1 is a cross-section of a first embodiment of tensiographic drophead according to the invention.

Referring to FIG. 1, a tensiographic drophead comprises a circularly symmetric quartz body 10 having a cylindrical outer surface 12 and a central through bore 14 coaxial with the axis of the body 10. A peripheral rebate 16 is formed around the lower end of the body 10 to define a terminal surface 18. The body 10 is manufactured so that, to a high degree of precision, the terminal surface 18 is circular, planar (flat), normal to and concentric with the axis of the bore 14, and has a sharply defined right-angled peripheral edge 20. It should be pointed out that the rebate 16 is provided in this embodiment simply to allow the drophead to be supported at its base without the support means (not shown) contacting the surface 18 or its peripheral edge 20. If the drophead were supported further up the body 10 the recess 16 would not be necessary and the surface 18 could extend fully to the surface 12, although it and its peripheral edge 20 would still need to be manufactured to a high degree of precision as described above.

Figure 1A:
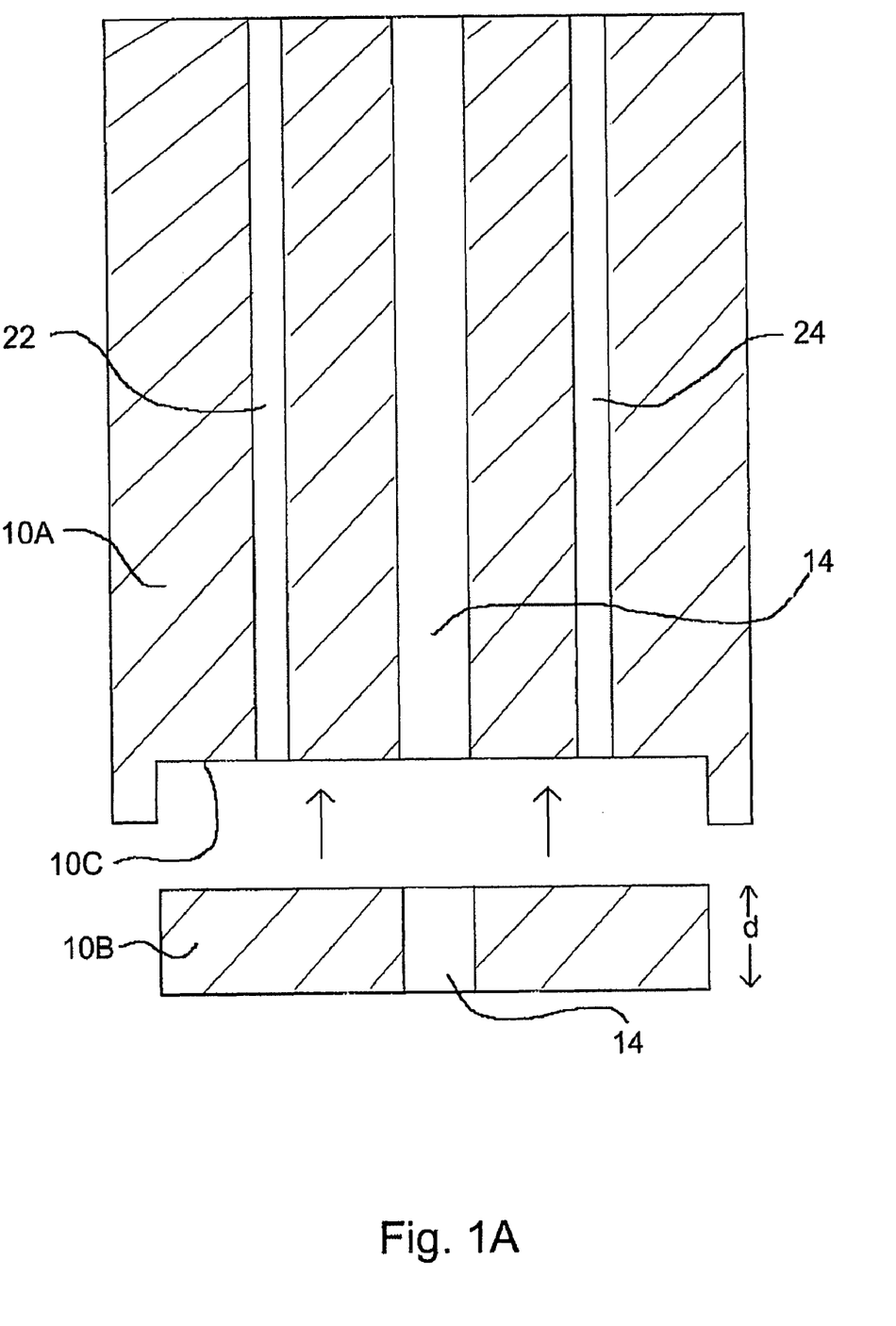
FIG. 1A illustrates one way of manufacturing the drophead of FIG. 1.

First and second blind bores 22, 24 are formed in the body 10. The bores terminate a distance d above the terminal surface 18—the significance of this will be explained later. The bores 22, 24 have mutually parallel axes and are disposed equidistant from and on diametrically opposite sides of the through bore 14. The drop head is conveniently manufactured in two parts 10A and 10B, FIG. 1A, where the part 10B is a quartz disk of thickness d which is heat and pressure fused into a circular recess 10C in the base of the part 10A. This allows the blind bores 22 and 24 to be formed throughout the full depth of the part 10A before the part 10B is fused thereto. The bores 14, 22 and 24 can be manufactured by laser or water jet drilling or other high precision manufacturing method. Although quartz is the preferred material of the body 10 because it is readily transmissive of UV, IR and visible light, the body 10 could alternatively be manufactured from a polymeric material which is transmissive of IR, UV and visible light at least in the range 200 nm-1500 nm which is the range of wavelengths primarily of interest.

In use, optical fibres 26 and 28 are inserted into the bores 22 and 24 respectively and pushed down until they abut the blind base of each bore. A small quantity of index matching oil is placed in the base of each bore 22, 24 so that there is no optical discontinuity between the fibres and the body 10. The fibres 26, 28 are a close fit in their respective bores 22, 24. A liquid feed pipe 30 is fitted to the top end of the central bore 14 so that liquid can be fed down to the terminal or lower surface 18 to form a static or dynamic drop 32.

The drophead can also be inverted so that the drop is formed as a sessile (or sitting) drop which is supported from below by the terminal surface rather than a pendant (or hanging) drop which is supported from above and hangs from the terminal surface. In such cases the liquid feed bore can be used to suck the drop volume out of the drophead and thereby clear the drop sample from the drophead. For sessile drops with an inverted drophead, the volume can (if desired) be added to the drophead from above using a syringe or some other liquid deposition means, so that the liquid feed tube is only used to withdraw volume out of the drophead.

The fibre 26 corresponds to the fibre 10 in FIG. 1 of U.S. Pat. No. 4,910,402 and is used to inject light (which, it will be recalled, in this specification includes IR and UV) into the drop 32, and is herein referred to as the source fibre. The fibre 28 corresponds to the fibre 11 in FIG. 1 of U.S. Pat. No. 4,910,402 and is used to collect light reflected internally in the drop 32, and is herein referred to as the collector fibre. The pipe 30 and bore 14 together correspond to the liquid feed pipe 14 in FIG. 1 of U.S. Pat. No. 4,910,402, and the bore 14 of the present specification is herein referred to as the liquid feed bore.

The surface 18 of the present drophead does not have an equivalent in the drophead of U.S. Pat. No. 4,910,402, where the drops simply hung from the ends of the fibres. In the present drophead, however, the bore 14 feeds the liquid under test to the lower surface 18 (in the normal configuration rather than the inverted one mentioned earlier) where the liquid spreads out to form a drop whose outer edges are coincident with and are suspended from the peripheral edge 20. For this reason the peripheral edge 20 of the lower surface can also be referred to herein as a suspension edge.

The drophead shown in FIG. 1 can be used in place of the drophead shown in FIG. 3 of U.S. Pat. No. 4,910,402 to make all the same measurements as are already described in that specification, and which do not need repeating here. Suffice to say that those measurements can be made to a higher degree of accuracy and reproducibility using the present drophead. However, the present drophead allows new measurements to be made which cannot be made, or at least cannot readily be made, with the prior drophead. This is entirely due to the fact that the ends of the optical fibres terminate above the plane containing the suspension edge 20.

We have found that by a suitable choice of drophead dimensions, an example of which will be given below, for most liquids, and in particular for water, alcohol and aqueous and alcohol solutions, although not limited to these, the intensity of the reflected light in a quasi-static, drop has a significant second order reflection peak. By a quasi-static drop we mean a drop which increases in volume slowly up to the point where it separates from (drops off) the drophead, or a drop which decreases slowly in volume as it is sucked back from the drophead (which can occur in either the normal or the inverted configuration).

Figure 2:
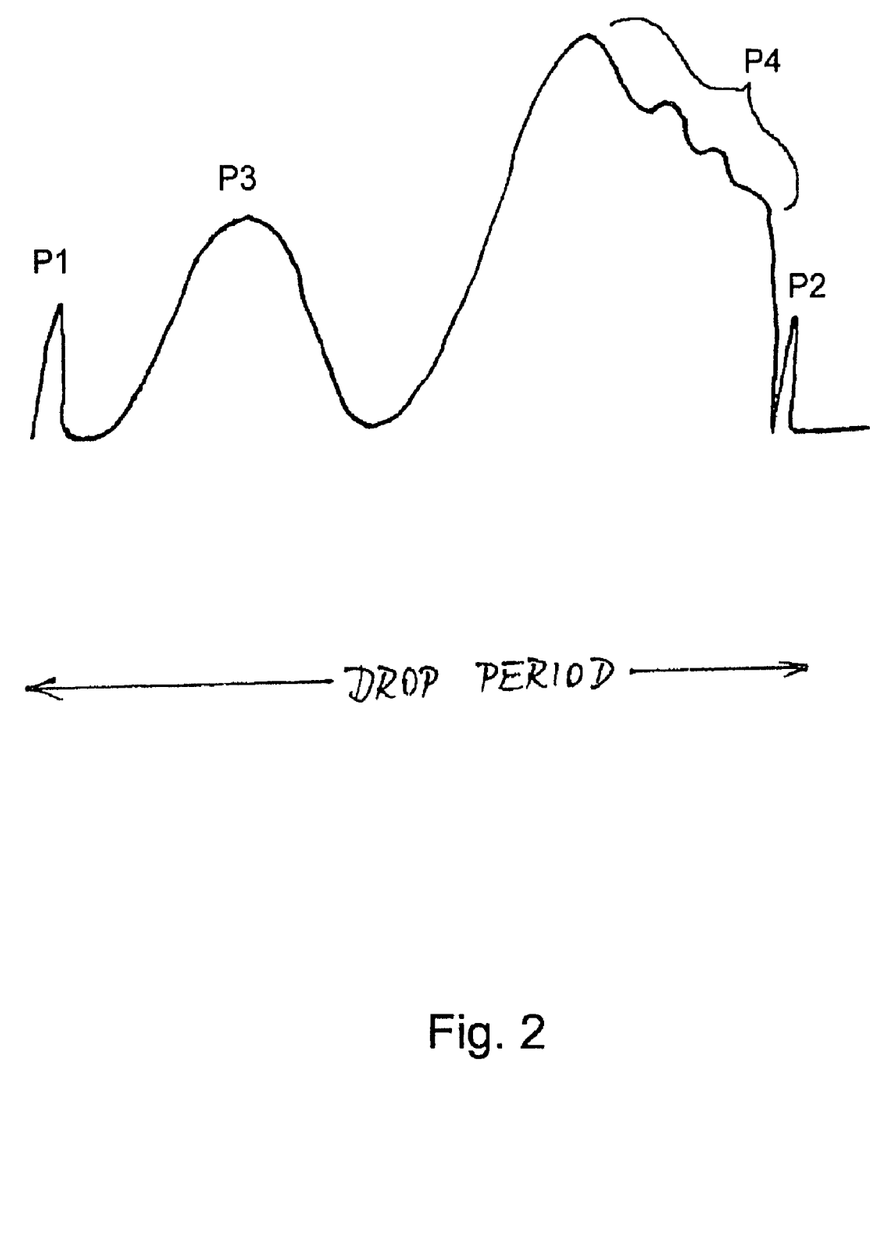
FIG. 2 is a typical tensiotrace obtained using the drophead of FIG. 1.

FIG. 2 is a graph of a typical tensiotrace obtained using the drophead of FIG. 1. The trace is obtained by pumping liquid under test at a uniform rate to the surface 18 via the liquid feed bore 14 using a motor stepper pump. The surface 18 supports the growing drop 32 until the gravitational forces overcome the surface forces acting on the drop and attaching it to the suspension edge 20, at which point drop separation occurs. Throughout the lifetime of the drop, light from an LED is injected into the drop through the source fibre 26. The reflected light is picked up by the collector fibre 28 and transmitted to a photodiode. The trace shown in FIG. 2 is essentially the amplified output of the photodiode and covers a single drop period bounded by separation peaks P1 and P2 (these are the well-known "blips" that occur as the drop separates from the drophead).

As can be seen, the trace exhibits a significant second order reflection peak P3 whose height and position are measurable to a high degree of accuracy (a second order reflection peak is one obtained by two internal reflections within the drop, as indicated by the ray R in FIG. 1). Where the lower ends of the light fibres 26 and 28 are substantially coincident with the plane containing the suspension edge 20, no second order reflection peak P3 is obtained or, if it is, it is low and ill-defined. The trace also shows the conventional third and subsequent order reflection peaks P4 but these again are ill-defined. (See the description of FIG. 19 at the end of this description for a discussion of first, second, third, etc. order reflections).

Preliminary tests showed that the following dimensions for the body 10 provide a drophead which gives a good, well-defined second order reflection peak for a wide range of liquids and light wavelength:

| | |
|---|---|
| Diameter of surface 18: | 9.0 mm |
| Diameter of liquid feed bore 14: | 1.7 mm |
| Diameter of bores 22, 24 and fibres 26, 28: | 1.0 mm |
| Distance d of fibre ends above surface 18: | 2.5 mm |
| Axial separation of bores 22, 24: | 4.0 mm |

However, the invention is not limited to those dimensions. In the discussion which follows below, some further results will be given for specific drophead dimensions when tested with specific liquids.

The height and position of the second order reflection peak P3 is very sensitive to the refractive index of the liquid, which gives possibilities for measurements not heretofore easily made.

Modifications of the drophead of FIG. 1 are possible. For example, since the "business end" of the drophead is that portion at and below the lower ends of the light fibres 26 and 28, except for their lower ends it is not strictly necessary that these light guides be parallel to each other or to the liquid feed bore 14, although clearly having them so makes for simpler manufacture.

Also, since the light only passes through the portion of the body 10 between the lower end of each light fibre 26, 28 and the lower surface 18, it is only necessary that the portion of the body 10 between the lower end of each light fibre and the lower surface be made of a material transmissive of UV, visible and IR light. However, once again, ease of manufacture means that at least the entire part 10B be made of quartz or other UV, visible and IR light transmissive material. It is also not necessary that the light fibres terminate the same distance above the surface 18 but, again, manufacturing considerations make this desirable.

Designs are also possible wherein the light fibres 26, 28 are not equidistant from the liquid feed bore 14, and/or not on diametrically opposite sides thereof. They also may not be parallel to the liquid feed bore 14, but skewed with respect thereto. There may also be more than two light fibres, and indeed the body 10, above the part 10B, could be composed of a bundle of parallel light fibres of which one or more serve as source fibres and one or more as collector fibres. In all cases, however, the source and collector light fibres terminate above the plane containing the suspension edge 20 in order to obtain a significant second order reflection peak (this is a necessary but not sufficient condition—other parameters will usually need to be adjusted empirically).

Figure 3:
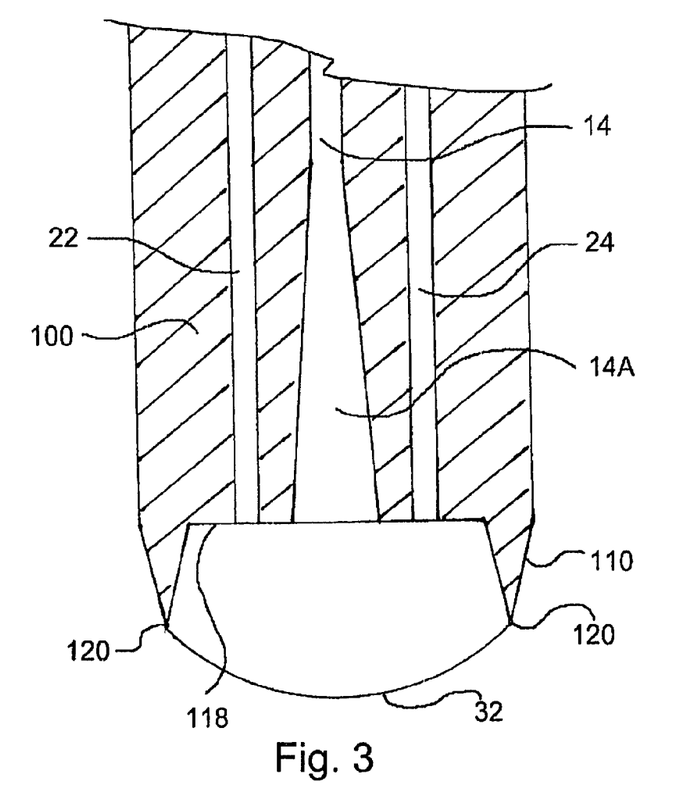
FIGS. 3-13 are each a cross-section of a further embodiment of tensiographic drophead according to the invention.

FIG. 3 is a cross-section of a second embodiment of drophead according to the invention (the light fibres 26, 28 and liquid feed pipe 30 are omitted). Like the first drophead, the quartz body 110 is circularly symmetric but in this case the lower surface 118 is recessed and bounded by a peripheral downwardly extending lip 110 whose lower edge 120 forms the suspension edge for the drop 32. The suspension edge 120 is a circular knife edge lying in a common plane. In this case the source and collector fibres terminate flush with the recessed lower surface 118 but this is not strictly necessary provided each terminates above the plane containing the suspension edge 120. It will be noted that the lower end 14A of the liquid feed bore 14 is conical so as to have an increasing diameter towards the surface 118. This enhances the spreading of the liquid throughout the recess and reliably ensures that the drop comes to hang on the edge 120.

Figure 4:
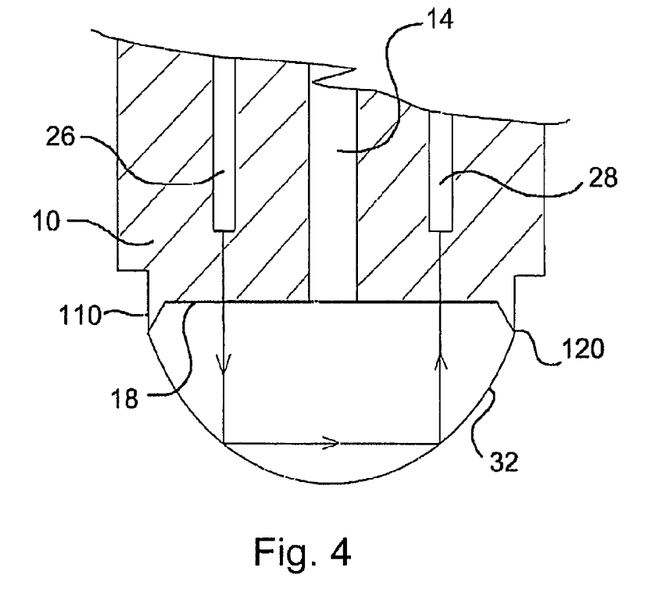

As seen in FIG. 4, the embodiment of FIG. 1 could also be provided with a peripheral downwardly extending lip 110 whose lower edge 120 forms the suspension edge for the drop 32.

Figure 5:
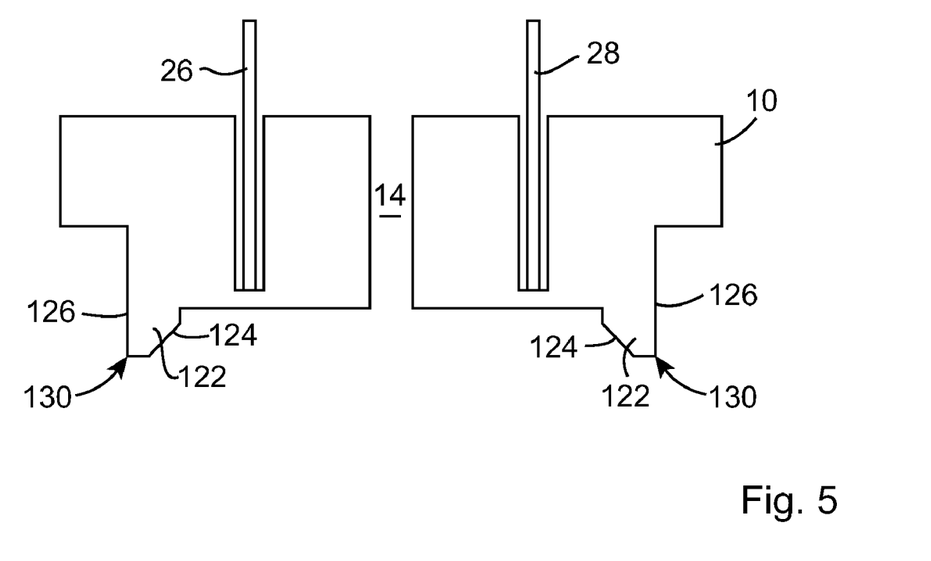

FIG. 5 shows a variation in which a peripheral downwardly extending lip 122 is chamfered on its inner surface 124 but not its outer surface 126, which results in a drop (not shown) which builds up on the recessed surface 128 spreading out to the outer peripheral edge 130 of the lip 122.

Figure 6:
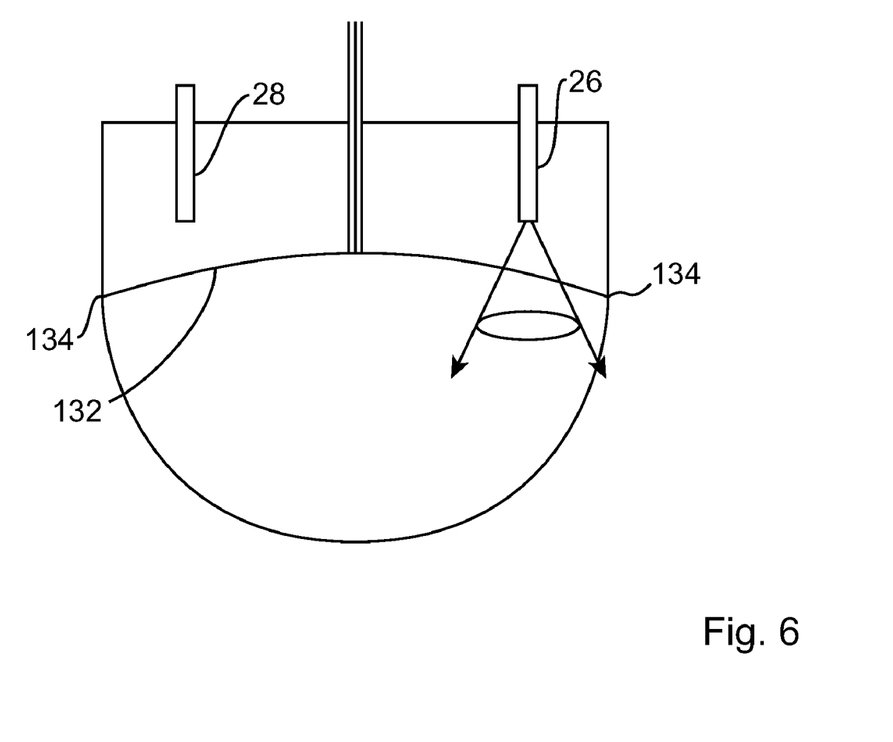

As shown in FIG. 6, a further embodiment has a concave terminal surface 132 bounded by a circular edge 134. The drophead is dimensioned so that the light cone 136 from the source fiber 26 illuminates a useful amount of the drop interior (e.g. if the source fiber were moved closer to the outside or the centre of the drophead, then the proportion of light impinging on the surface of the drop at angles not giving rise to total internal reflection would vary, and so the drophead will be dimensioned to take account of the particular liquid being tested and the wavelength of light employed).

Figure 7:
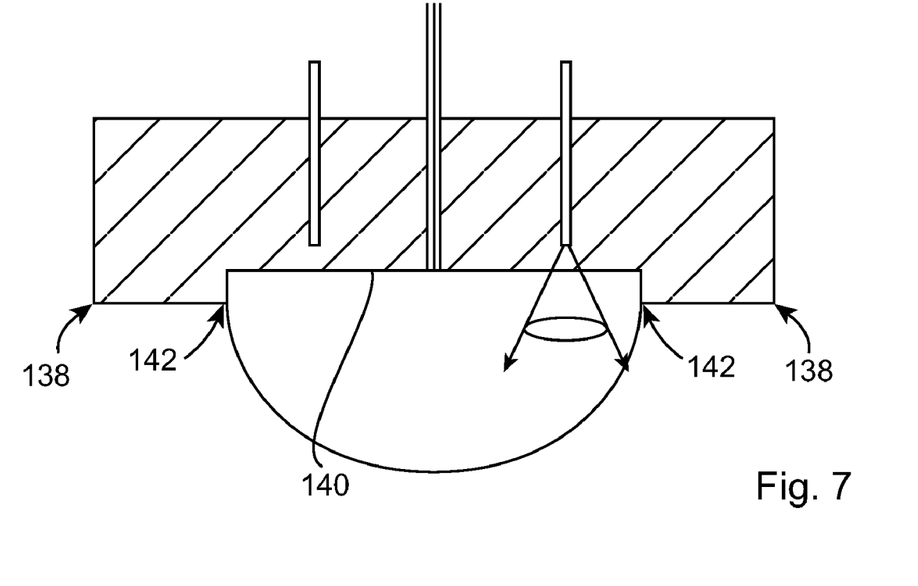

FIG. 7 shows a drophead which is in some ways similar to the embodiment of FIG. 5, but without the chamfer. In the case of this drophead, liquid does not spread out to the outermost edge 138 of the drophead, and so the peripheral or suspension edge of the terminal surface 140 is the edge 142.

Figure 8:
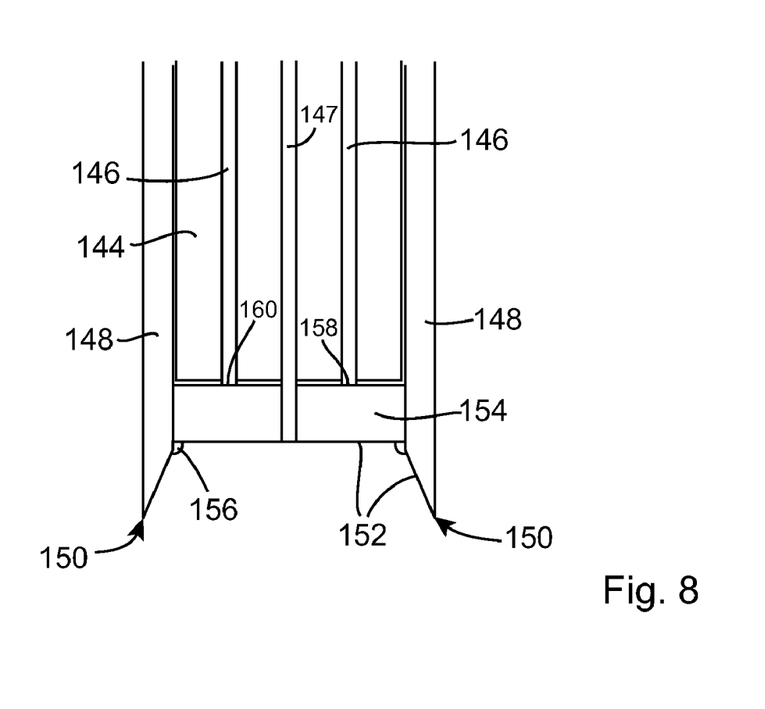

FIG. 8 is a composite drophead in which a relatively cheap and easily machined cylinder 144 made of metal or plastic (possibly opaque) is used to support the fibers 146 and the liquid feed bore 147. A cylindrical stainless steel sleeve 148 (chosen for its inert properties and its ease of machining to a precise shape) is positioned around the cylinder 144. Sleeve 148 has a knife edge 150 which acts as a peripheral or suspension edge of the lower surface 152 of the drophead. A quartz disk 154 is held within the sleeve 148 by adhesive 156 and defines part of the terminal surface. It can be seen that liquid bore 147 extends through the quartz disk but that the transmission surface 158 (i.e. the termination of the source fiber) and the collection surface 160 (i.e. the termination of the detection fiber) stop at the top of the quartz disk.

FIGS. 9-12 show a number of variations on the light source and light detector.

Figures 9, 11:
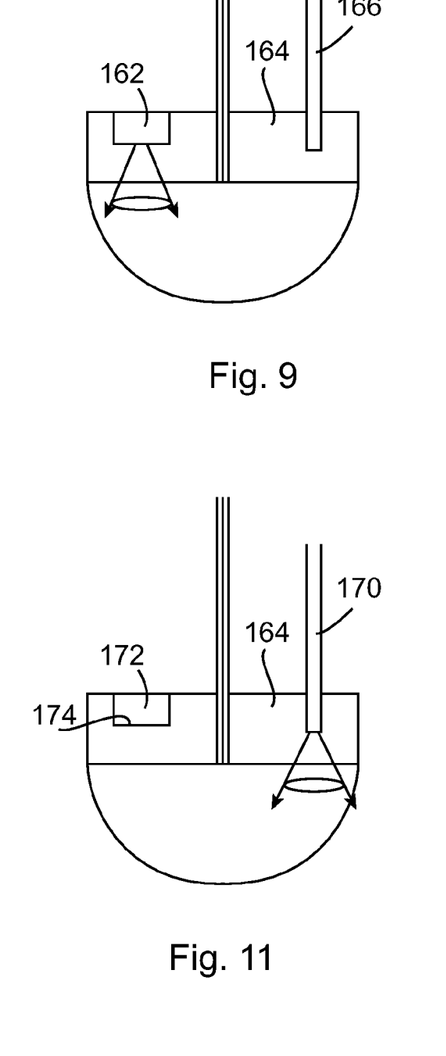

In FIG. 9, the light source is a white LED 162 embedded in the quartz drophead 164 while the detector employs an optical fiber 166 leading to a conventional charge coupled device, a photocell or any other suitable detector (not shown).

Figures 10, 12:
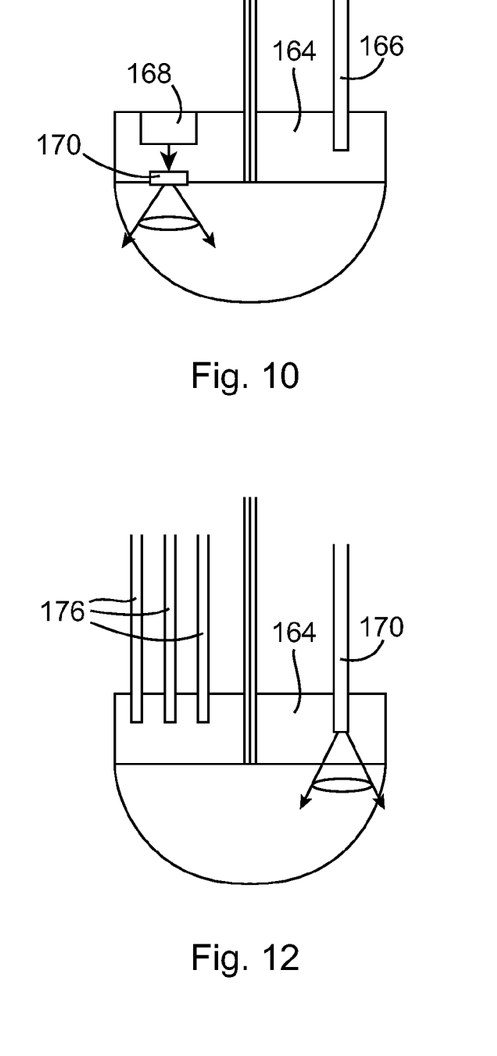

In FIG. 10, the source includes a laser 168 and a diffuser 170 working in conjunction to provide a light source. The detector is again an optical fiber 166 leading to a conventional detection system.

In FIG. 11, the source is a light fiber 170 connected to a conventional means of illumination (not shown) while the detector is a silicon-based or other solid state detector 172 embedded in the drophead 164. By employing, for example, a charge coupled device or a CMOS detector having a collection surface 174 which detects different light intensities at different positions, a greater amount of information can be elucidated about the characteristics of the liquid under test than if one simply collects light with the collection surface of a fiber termination (which approximates to a point detector). The light pattern from the source fiber 170 reflects back onto the drophead to produce a pattern of light which is far more informative than a single point intensity. The whole pattern is useful for diagnosing the qualitative properties of the liquid under test, while quantification is of course possible using the specific pixel location(s) on the CCD or CMOS.

Similarly, the system shown in FIG. 12 employs not one but rather a plurality of detector fibers, each leading to a separate detection system, so that the light intensity at a number of points can be measured.

Figure 13:
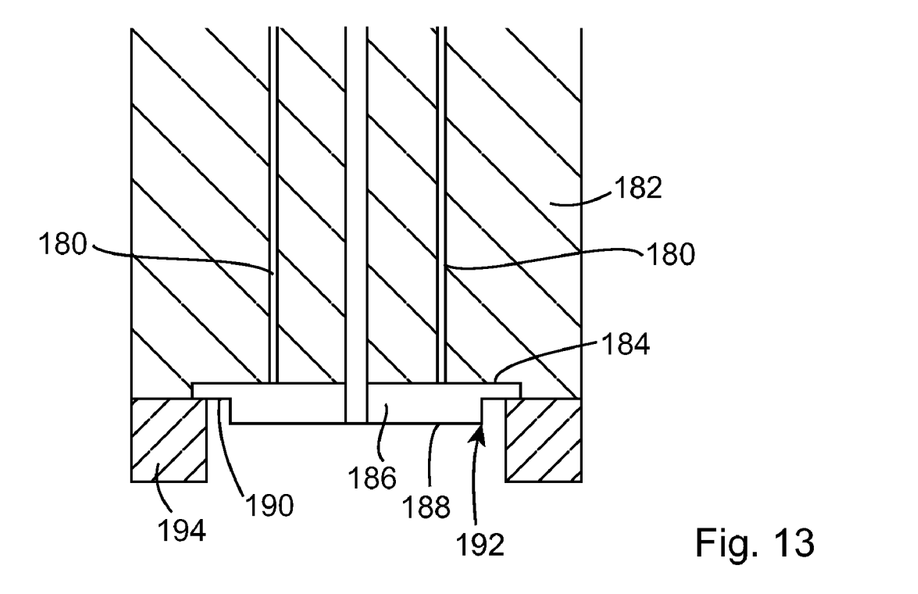

A further composite drophead is shown in FIG. 13, in which the source and detection fibers 180 are carried in a brass cylinder 182 having a shallow recess 184 which receives a quartz disk 186 with a protruding circular face 188 and a recessed periphery 190. The edge 192 of the protruding face 188 defines the peripheral or suspension edge for the drop. The disk 186 is held in position using a brass ring 194 firmly connected to the brass cylinder (such as by a screw thread fixing mechanism, not shown).

In order to determine the optimum dimensions for a drophead in some specific situations, a simulation was carried out. A model of a drophead with a flat lower surface and in which the light source and detectors, represented by optical fibers, was simulated, and the simulation was tested. The passage of rays of light through the complete system—input fibre, drophead, multiple reflections in the drop, back through the drophead, and finally into the exit fibre—were followed, including all intensity losses at each interface, in order to provide a simulation of the response of the system. The calculations were carried out for both water and ethanol.

1. Parameters

Simulations of the way in which the system responds to variations in the following parameters were modelled for both water and ethanol:

$r_0$=drophead radius
xpos=offset of fibre centres from centre line of the head
zpos=position of fibres above bottom of drop head
The full specifications of the input parameters were:

| Material parameters | Water | Ethanol | Remarks |
|---|---|---|---|
| surfT | 73.05 | 24.05 | Surface tension in dynes/cm |
| rho | .9986 | .7911 | density in $g/cm^3$ |
| rindex | 1.333 | 1.359 | ref. index |
| alpha | 0. | 0. | attenuation in $cm^{-1}$ |

| Drophead parameters | Values | Variations | Remarks |
|---|---|---|---|
| ncore | 1.49 | | fibre core refractive index |
| nclad | 1.4433 | | fibre cladding refractive index, gives NA = 0.37 |
| nhead | 1.54 | | Refractive index of drophead, for quartz |
| r0 | 4.0 | 2.5-4.0 | drophead radius in mm |
| fibrad | .5 | | radius of fibres in mm |
| posin0(1:3) | 2.0, 0.0, 0.2 | (1.5-3, 0, .1-.4) | input fibre position in mm (x, y, z) |
| posout0(1:3) | −2.0, 0.0, 0.2 | (−1.5-3, 0, .1-.4) | output fibre position in mm* |

| Modelling parameters | Values | Remarks |
|---|---|---|
| x0min | 0.5 | x0 = normalised radius at bottom |
| x0max | 2.5 | |
| dx0 | 0.005 | increment in x0 |

-continued

| nth | 500 | no. of θ-values** |
| irand | 1 | for random position over fibre |
| rrandrel | 1 | relative radius of random position |
| stopindex0 | 0 | (for testing) |

*The detector fibre always has the same zpos as the input fibre, but the xpos value is opposite in sign (ypos is always 0, meaning that the fibers lie on a common diameter of the drophead), so that the fibres are symmetrical about the centre of the drophead.
**This value produces 785146 rays for each data point.

The basic derived parameter that determines the drop shape is $$P0 = \rho g r 02/2T = rho * 981. * (r0/10.0) ** 2/(2. * surfT).$$

For $r_0 = 4$ mm, $P_0 = 1.0728$ (water), 2.5815 (ethanol).

Thus, the drop shapes for water with a drophead radius of $r_0 = 4$ mm are the same as ethanol with $r_0 = 2.58$ mm.

Figure 14:
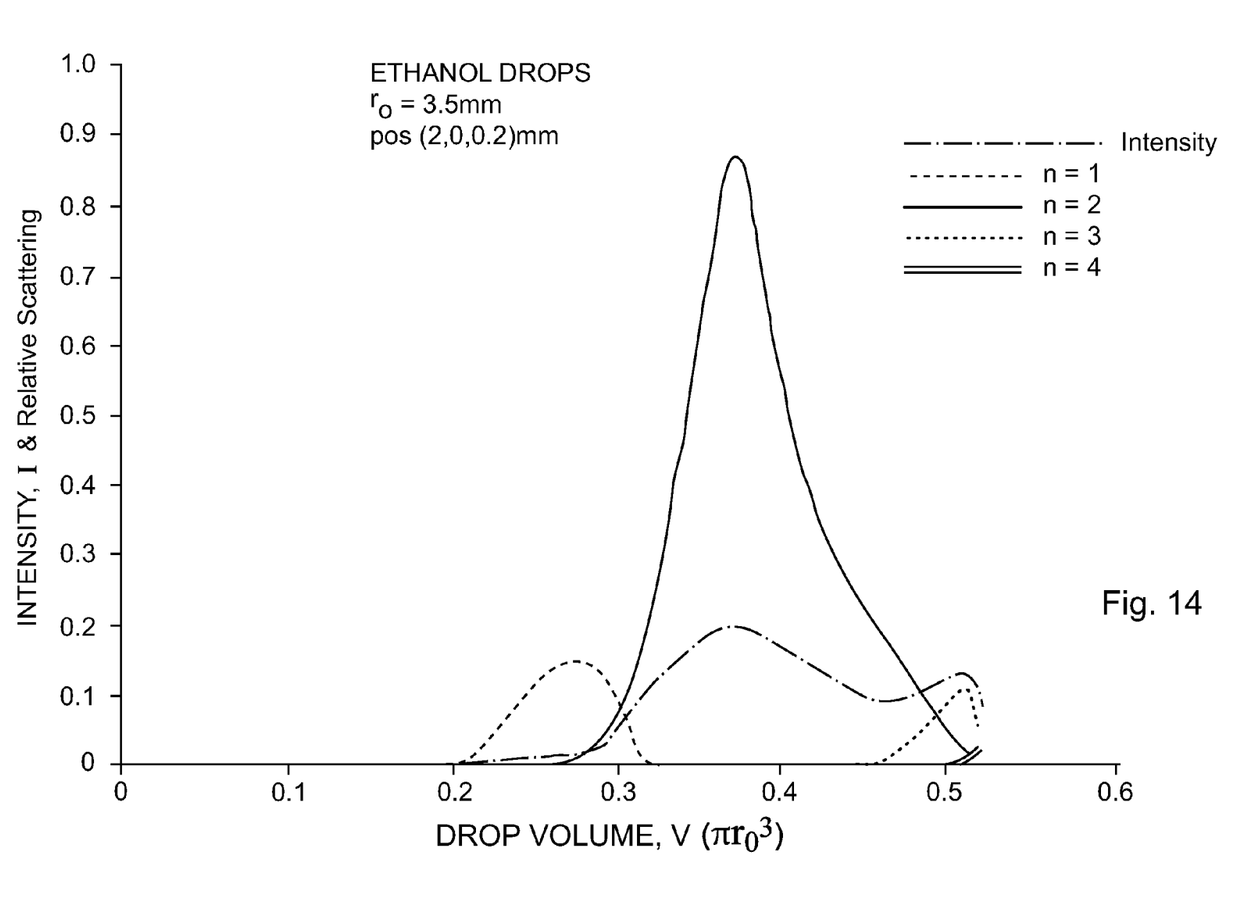
FIG. 14 is an output of a simulation to model the performance of a drophead with a particular set of dimensional parameters.

FIG. 14 shows an output of the simulation for ethanol with the parameters indicated on the drawings. The "dot-dash" line shows the intensity I (at the detector, relative to unit intensity in the input fibre) vs. scaled drop volume V (in units relative to $\pi r_0^3$). From this it can be seen that the maximum throughput is about 20%.

In addition, the graph shows the relative number of detected rays that have undergone n reflections (n=1, 2, 3, 4), and the sum of all these relative numbers. These latter plots do not include the intensity losses that occur between the fibre and the head, from head to drop, and at the surface of the drop.

Note that the n=1 reflection is very weak (and indeed other simulations showed that it does not occur at all for some values of $r_0$, xpos and zpos). The dominant reflection here is the n=2 reflection. Around 87% of all rays at relative volume V~0.37 are detected after 2 reflections, each with around 30% transmission, so that the peak intensity I at this volume is 0.2. The n=3 reflections, which appear just near the end of the trace at V~0.5, are relatively less probable than the n=2 reflections at V~0.37, but their transmission is higher because the angles of incidence on the drop surface are greater, so the reflectivity is greater. The n=4 reflections are barely measured and the n=5 plot (not shown) was omitted because it was in effect zero.

Intensity is observed above a minimum volume V~0.2. This value appears to be applicable over a wide range of conditions. The plots terminate at the maximum volume for given $r_0$. The drop shapes and the maximum volume depend only on the parameter $P_0$. However, the detected intensity will depend also on the material parameters, which determine the transmission losses, and on the positioning of the fibres.

Figure 15:
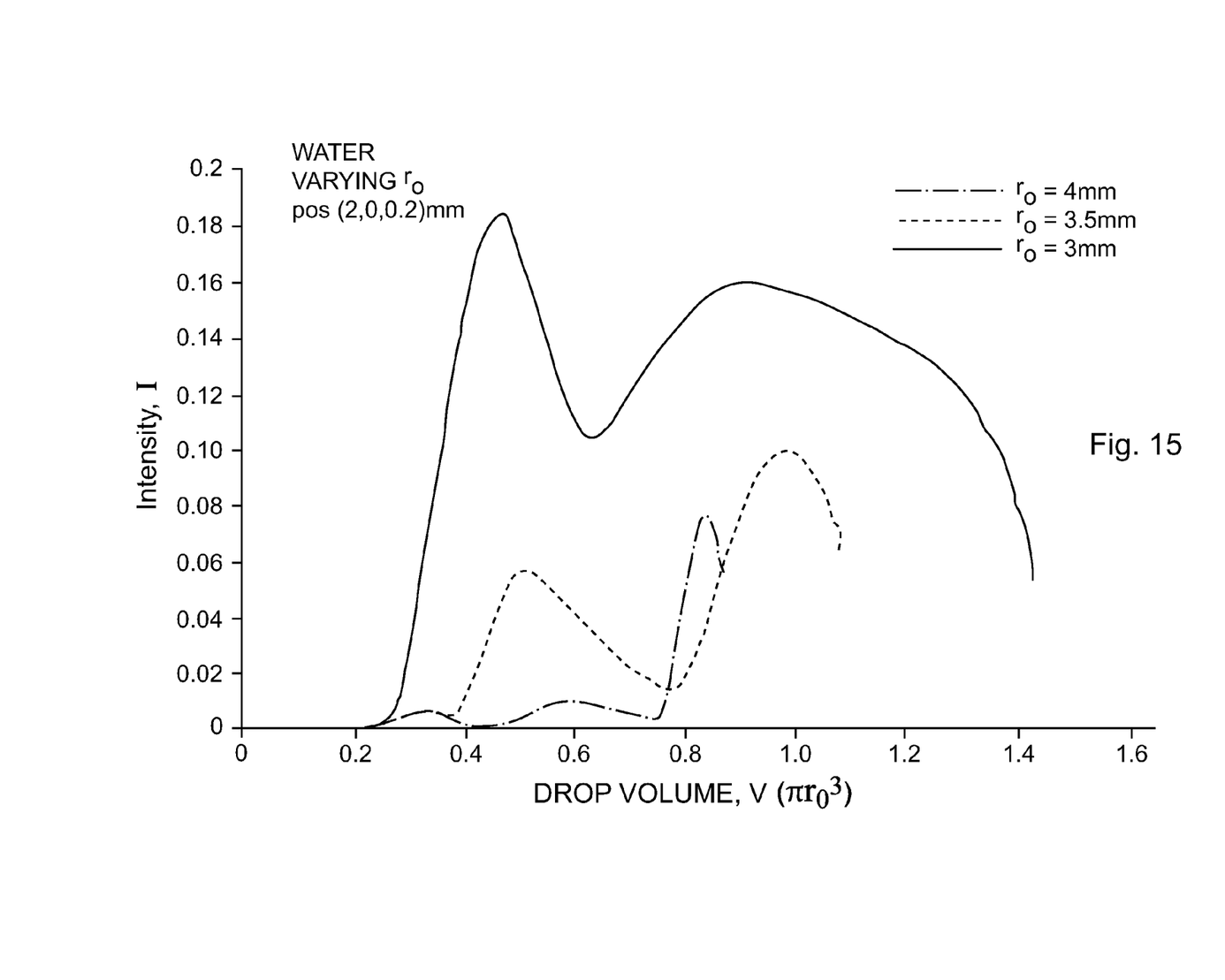
FIGS. 15 and 16 show the effect on the model of varying the drophead radius for water and ethanol drops, respectively.
Figure 16:
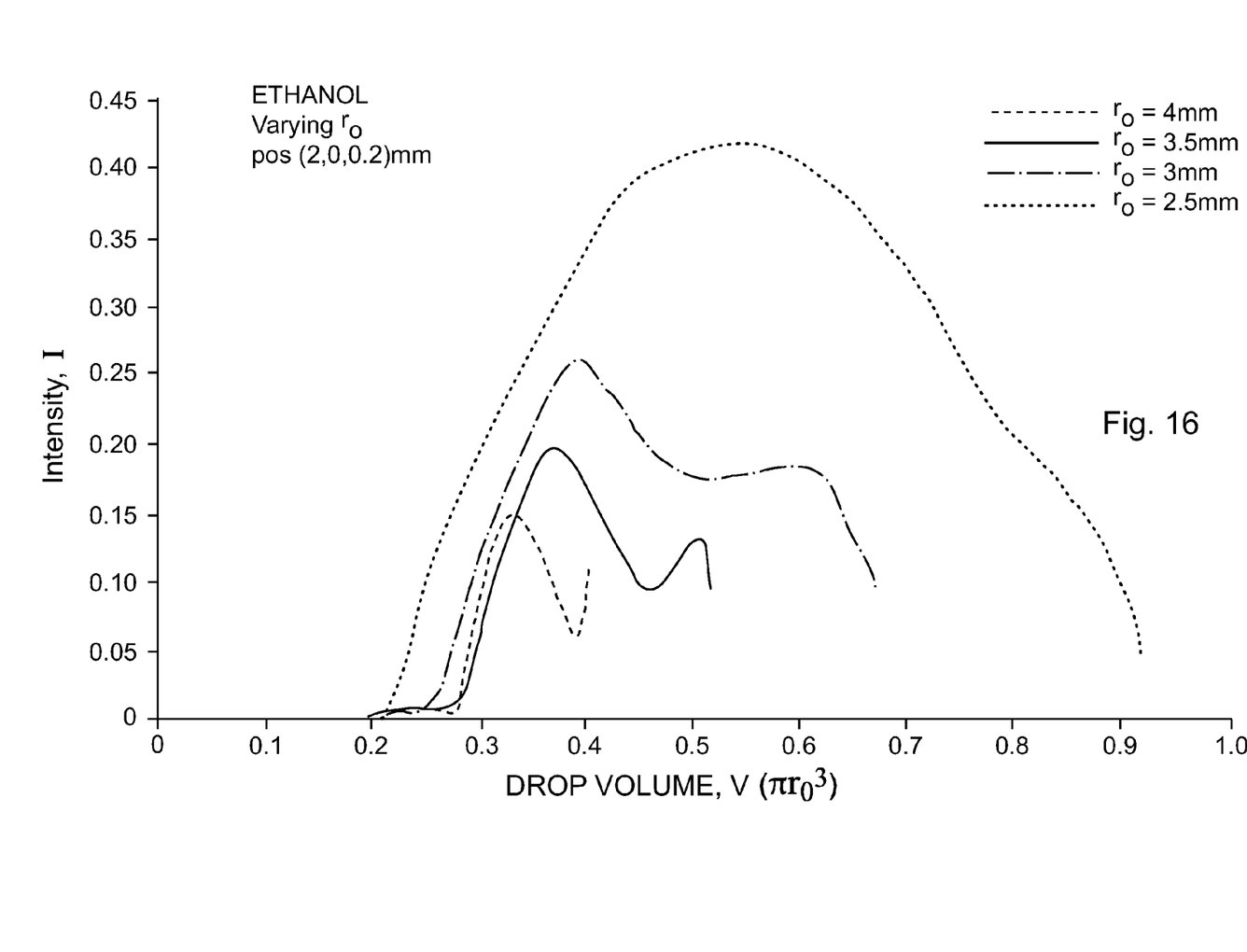

In FIGS. 15 and 16, The radius r0 of the head is varied, keeping xpos=2 mm, zpos=0.2 mm.

The graph of FIG. 15 shows I vs. V for water, varying r0 (=4, 3.5 and 3 mm). When r0=4 mm, the M=1, 2 and 3 peaks are clearly resolved. At r0=3 mm, the dominant first peak has M=2, and whilst the second peak has M=3, higher order reflections contribute noticeably above V~1.0. By the end of the trace, the dominant reflections have M=5, but there are significant contributions from M=8 and higher. The clearest structure is obtained around r0=3.5 mm.

For ethanol (FIG. 16), the clearest structure is observed around r0=3 to 3.5 mm. At r0=2.5 mm (P0=1.00), there is no definable structure. This value of P0 is virtually the same as for water with r0=4 mm (P0=1.07), so the drop shapes are the same in the two cases. The difference in traces is because the absolute fibre positions and sizes are the same in the two cases, and are relatively so large for ethanol at r0=2.5 mm that most of the resolution is lost. No doubt the two cases would be much more similar if the fibre sizes and positions were scaled with r0, but that is not what is done experimentally.

Figure 17:
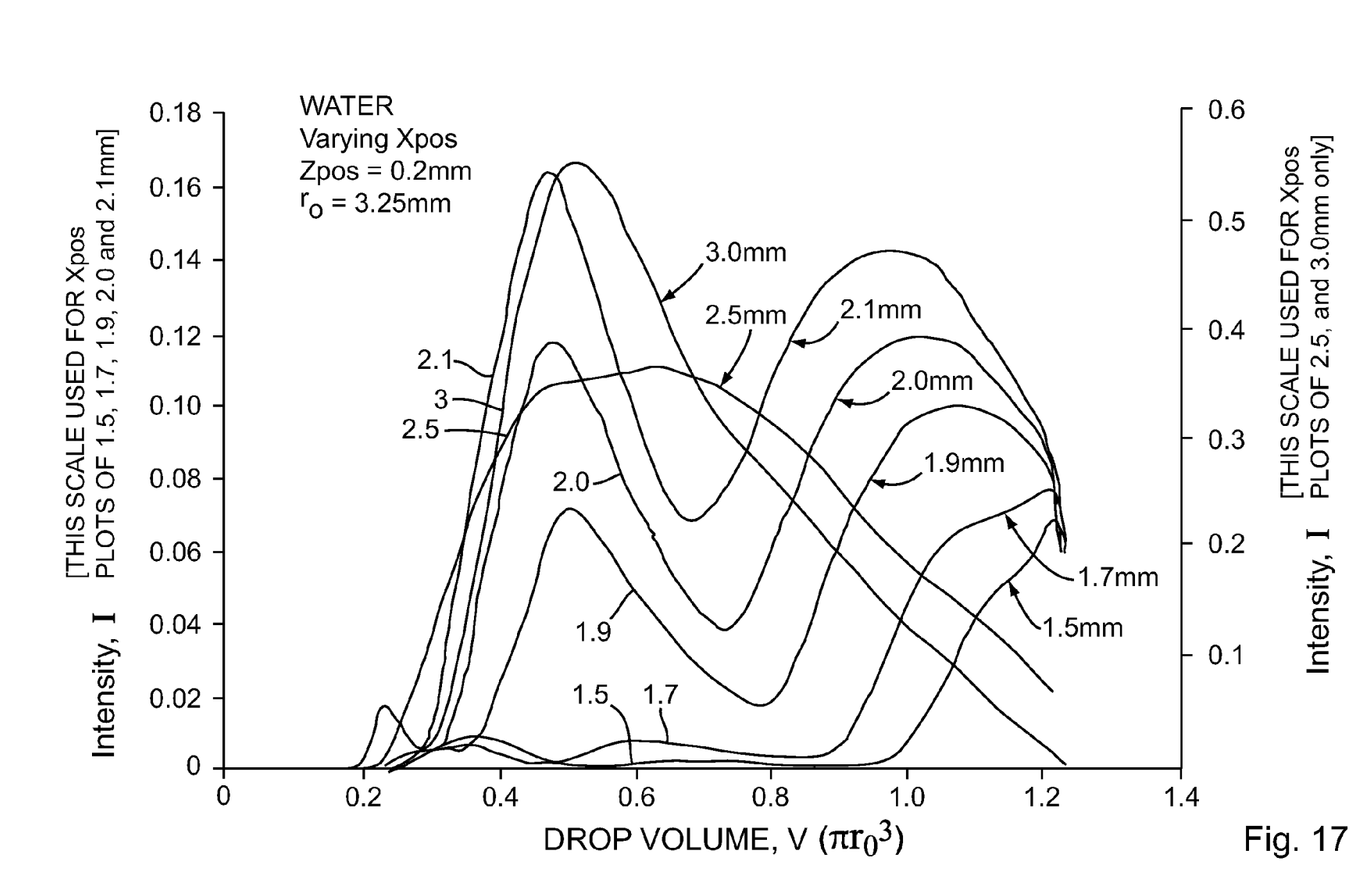
FIGS. 17 and 18 show the effect on the model of varying the lateral position of the source and detector fibers for water and ethanol drops, respectively.
Figure 18:
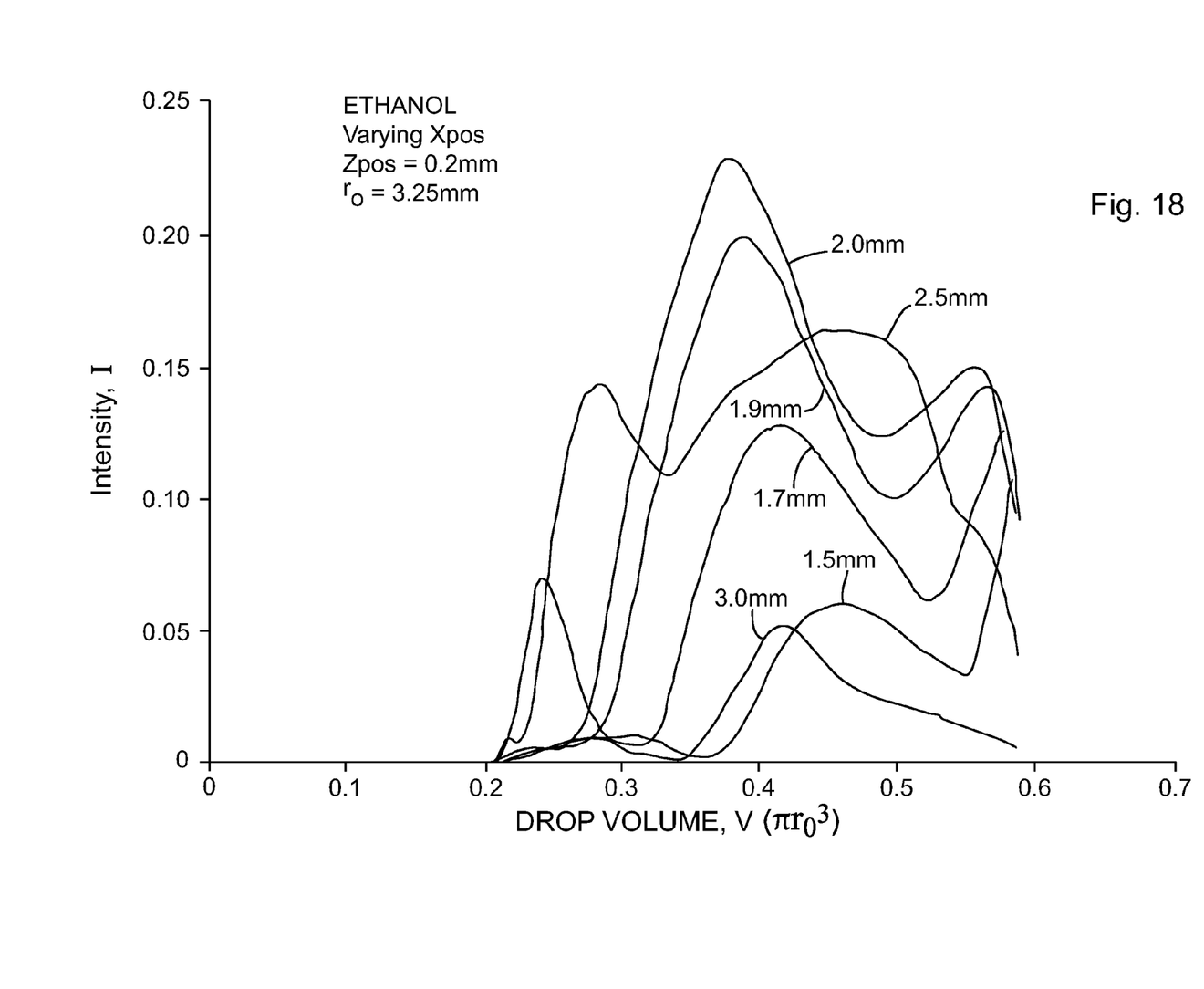

Next the effect of variation of xpos was measured. FIGS. 17 and 18 show the results for water and ethanol, respectively.

For water (FIG. 17), the optimum appears to be around xpos=2 mm. There is a loss of intensity below this value; above it, the structure is less well-defined (note that the scale for the graphs with the two largest xpos values, 2.5 and 3 mm, is on the right).

For ethanol (FIG. 18), the optimum value for xpos appears to be around 1.9 mm. Note that there is a maximum in the throughput around 2 mm, unlike the case for water, where the signal increases with increasing xpos.

Similar tests were carried out when keeping xpos constant at a value of 2 mm but varying zpos, but the results (not shown) indicated that the shapes were essentially unaffected and that zpos is not as critical to signal as xpos.

Conclusions

The optimum responses for both water and ethanol were obtained around the following values:
$r_0 = 3.25$ mm (i.e. head diameter 6.5 mm)
xpos=2 mm
zpos is nowhere near as critical as the other two parameters; the smaller zpos, the better the throughput.

This result agrees well with experiments conducted on test dropheads.

Figure 19:
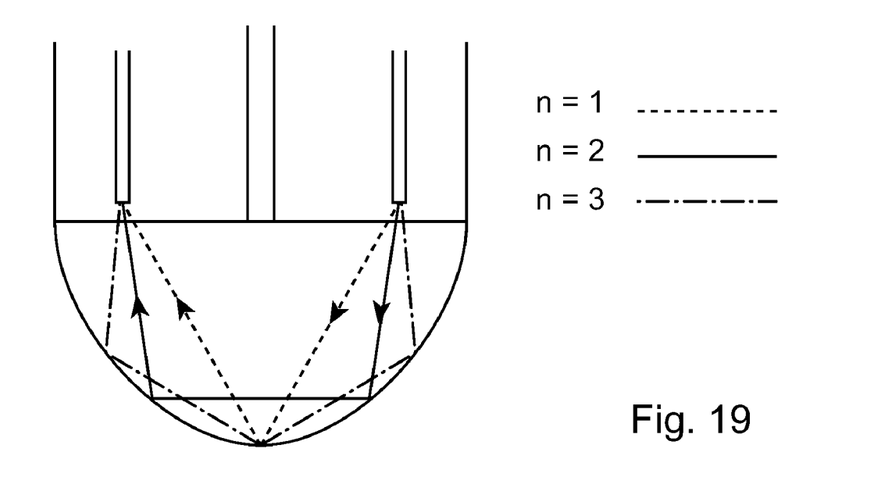
FIG. 19 is a schematic ray diagram which shows the first, second and third order reflections within a drop volume.

FIG. 19 shows a schematic ray diagram of a drop with three rays traced within the drop undergoing total internal reflection. The first ray, shown by the regular dashed line, is the n=1 or first order reflection, where the light reflects just once between the source fiber 26 and the detector fiber 28.

The second order reflection is shown by the solid line (n=2). It will be appreciated that the light will emerge in a cone and so there is not just a single path of reflection within a three dimensional drop, but rather a set of paths which will give the reflection for any given drop size and shape. Similarly, the third order reflection is shown (n=3) using the "dot-dash" line.

The invention is not limited to the embodiments described herein which may be modified or varied without departing from the scope of the invention.

The invention claimed is:

1. A tensiographic drophead comprising a body having a terminal surface with a peripheral edge substantially disposed in a plane, a liquid feed bore extending through the body to the terminal surface for transporting liquid to or from the terminal surface to thereby control, in use, the volume of a drop whose outer edges are defined by the peripheral edge, a light source for transmitting light into the drop, said light source having a transmission surface, and a light detector for collecting light reflected internally from the drop back to the drophead, said light detector having a collection surface, wherein the transmission surface and the collection surface are each disposed in the drophead and are each spaced apart from said plane of said peripheral edge, wherein the transmission surface terminates within the body short of the terminal surface, and wherein at least the portion of the body between the transmission surface and the terminal surface is made of a material transmissive of light.

2. A drophead as claimed in claim 1, wherein the transmission and collection surfaces are disposed substantially equidistant from and on diametrically opposite sides of the liquid feed bore.

3. A drophead as claimed in claim 1, wherein the transmission surface is a termination of a light guide.

4. A drophead as claimed in claim 1, wherein the detection surface is a termination of a light guide.

5. A drophead as claimed in claim 4, wherein the transmission surface is a termination of a light guide, and at least the lower ends of said light guides whose terminations provide said transmission and detection surfaces have substantially parallel axes normal to the plane containing the peripheral edge.

6. A drophead as claimed in claim 1, wherein the transmission surface is an emitting surface of a solid-state light source.

7. A drophead as claimed in claim 6 wherein the collection surface is a collection surface of a solid-state light detector.

8. A drophead as claimed in claim 1, wherein the collection surface terminates within the body short of the terminal surface, and wherein at least the portion of the body between the collection surface and the terminal surface is made of a material transmissive of light.

9. A drophead as claimed in claim 1, wherein said material is quartz.

10. A drophead as claimed in claim 1, wherein the terminal surface is substantially flat.

11. A drophead as claimed in claim 1, wherein the terminal surface is recessed and is bounded by a peripheral extending lip forming the peripheral edge.

12. A drophead as claimed in claim 11, wherein the light guides terminate substantially flush with the recessed terminal surface.

13. A drophead as claimed in claim 1, wherein the peripheral edge is substantially circular and concentric with the axis of the liquid feed bore.

14. A drophead as claimed in claim 1, wherein the transmission surface and the collection surface are each spaced apart from the plane of the peripheral edge by substantially the same distance.

15. A drophead as claimed in claim 1, further comprising a mounting system for mounting the drophead with said terminal surface facing downwardly and said plane substantially horizontal, such that a drop of liquid can be suspended in use from the terminal surface and the peripheral edge.

16. A drophead as claimed in claim 1, further comprising a mounting system for mounting the drophead with said terminal surface facing upwardly and said plane substantially horizontal, such that a drop of liquid can be supported in use above the terminal surface and the peripheral edge.

* * * * *